(12) United States Patent
Swann

(10) Patent No.: US 9,107,710 B1
(45) Date of Patent: Aug. 18, 2015

(54) BONE FIXATION ASSEMBLY

(71) Applicant: Alliance Partners, LLC, San Antonio, TX (US)

(72) Inventor: Karl W. Swann, San Antonio, TX (US)

(73) Assignee: Alliance Partners, LLC, San Antonio, TX (US)

( * ) Notice: Subject to any disclaimer, the term of this patent is extended or adjusted under 35 U.S.C. 154(b) by 216 days.

(21) Appl. No.: 13/758,522

(22) Filed: Feb. 4, 2013

Related U.S. Application Data

(60) Provisional application No. 61/594,111, filed on Feb. 2, 2012.

(51) Int. Cl.
*A61B 17/80* (2006.01)

(52) U.S. Cl.
CPC .................................. *A61B 17/8042* (2013.01)

(58) Field of Classification Search
CPC .................................................. A61B 17/8042
USPC .................................................. 606/294–295
See application file for complete search history.

(56) References Cited

U.S. PATENT DOCUMENTS

| | | |
|---|---|---|
| 8,216,285 B2 | 7/2012 | Markworth |
| 2006/0200146 A1 | 9/2006 | Doubler et al. |
| 2011/0106159 A1* | 5/2011 | Nazeck .......................... 606/246 |
| 2011/0319942 A1 | 12/2011 | Bottlang et al. |
| 2012/0010618 A1 | 1/2012 | Markworth |

\* cited by examiner

*Primary Examiner* — Andrew Yang
*Assistant Examiner* — Olivia C Chang
(74) *Attorney, Agent, or Firm* — Greenberg Traurig, LLP; Ross Spencer Garsson

(57) ABSTRACT

A bone fixation assembly comprising a bone fixation plate having an outer surface, a bone contact surface, and at least one bore sidewall defining at least one bore extending between the outer surface and the bone contact surface, the outer surface being located outwardly of the bone contact surface; at least one slot sidewall defining at least one slot formed in the bone fixation plate, the at least one slot being adjacent to the at least one bore sidewall and between the outer surface and the bone contact surface, the at least one slot having at least one slot passage adjacent to a corresponding bore and a slot opening adjacent to the slot passage; at least one stop formed by the at least one sidewall, the at least one stop positioned opposite of the slot passage from the corresponding bore; and at least one retaining member insertable into the at least one slot from the at least one bore, wherein the at least one retaining member is bendable between a normally-open position having a width greater than the width of the at least one slot passage and a closed position having a width less than the width of the slot passage.

9 Claims, 11 Drawing Sheets

BONE FIXATION ASSEMBLY

This application claims priority to and benefit of, and incorporates herein by reference, U.S. Provisional Patent Application Ser. No. 61/594,111, filed Feb. 2, 2012.

STATEMENT REGARDING FEDERALLY SPONSORED RESEARCH OR DEVELOPMENT

Not applicable.

BACKGROUND OF THE INVENTION

1. Field of the Invention

The present invention relates to medical devices. More specifically, the present invention is a bone fixation assembly for attachment between bones for stabilization.

2. Description of the Related Art

There are several bone fixation assemblies available in the industry that incorporate locking mechanism to prevent screw or anchor back out. Some of these systems have snap rings to cover screws, some system have screw covers, and some have threaded bores for engagement with the bone screw or anchor. Drawbacks of conventional systems include the complexity of the locking mechanism as well as locking mechanisms that secure more than one screw, so that if the locking mechanism fails, multiple screws could be left unsecured.

BRIEF SUMMARY OF THE INVENTION

The present invention provides an improved bone fixation assembly that incorporates a novel locking mechanism. The invention comprises a bone fixation plate having an outer surface, a bone contact surface, and at least one bore sidewall defining at least one bore extending between the outer surface and the bone contact surface, the outer surface being located outwardly of the bone contact surface; at least one slot sidewall defining at least one slot formed in the bone fixation plate, the at least one slot being adjacent to the at least one bore sidewall and between the outer surface and the bone contact surface, the at least one slot having at least one slot passage adjacent to a corresponding bore and a slot opening adjacent to the slot passage; at least one stop formed by the at least one sidewall, the at least one stop positioned opposite of the slot passage from the corresponding bore; and at least one retaining member insertable into the at least one slot from the at least one bore, wherein the at least one retaining member is bendable between a normally-open position having a width greater than the width of the at least one slot passage and a closed position having a width less than the width of the slot passage.

DETAILED DESCRIPTION OF THE EMBODIMENTS

Figure 1:
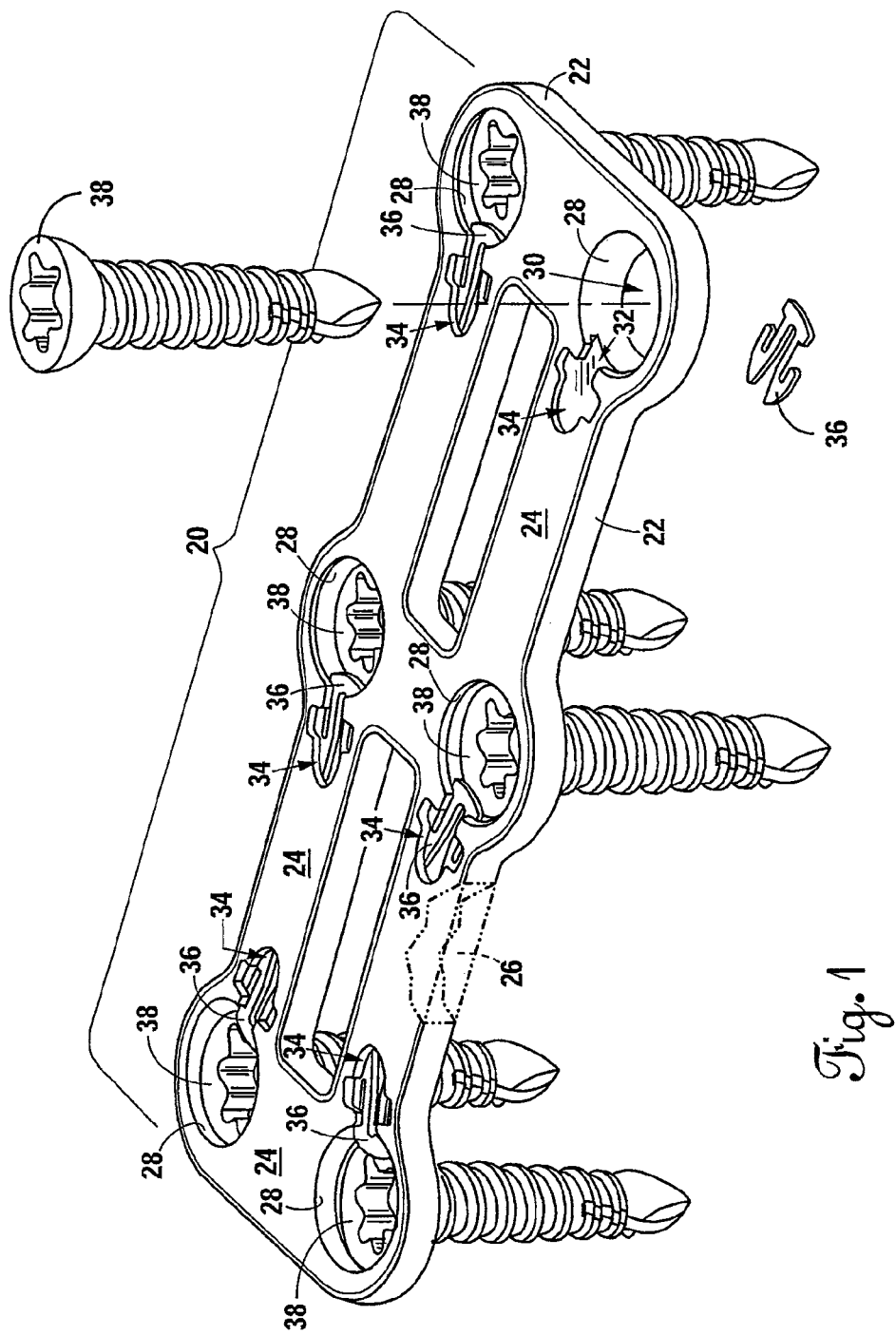
FIG. 1 is an isometric partial assembly view of an embodiment of the invention.

FIG. 1 is a partial assembly view of a bone fixation assembly 20 having the features of the invention. The assembly 20 includes a bone fixation plate 22 having an outer surface 24 and a bone contact surface 26 located inward (i.e., toward the bone) of the outer surface 24. The bone contact surface 26 is the primary contact surface between the assembly 20 and a patient's bone.

Bore sidewalls 28 define bores 30 extending through the plate 22 between the outer surface 24 and the bone contact surface 26. Each bore 30 has a corresponding slot 32 and access 34 formed in the bone fixation plate 22 adjacent to the bore 30 and extending radially away from the center axis of the bore 30 into the plate 22. Nitinol, also known as nickel titanium, is highly biocompatible, and can be used because of its superelastic characteristics. Nitinol exhibits enormous elasticity, some ten to thirty times that of ordinary metal.

Figure 2:
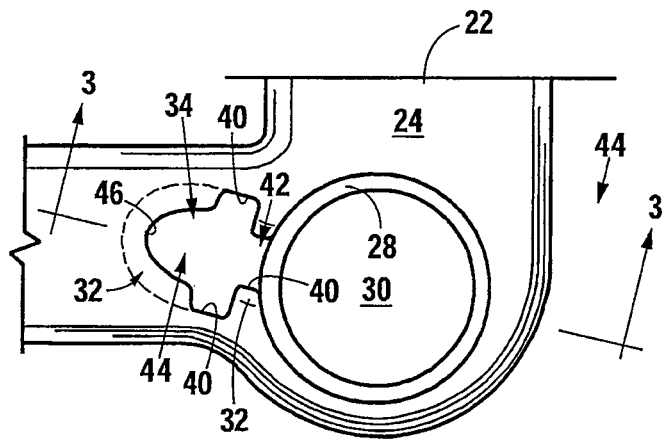
FIG. 2 is a top plan view of a portion of the bone plate of the embodiment shown in FIG. 1.
Figure 3:
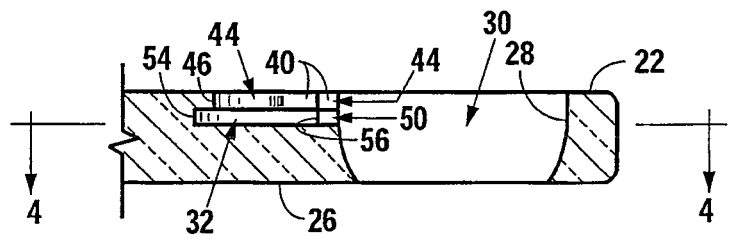
FIG. 3 is a sectional view through line 3-3 of FIG. 2.
Figure 4:
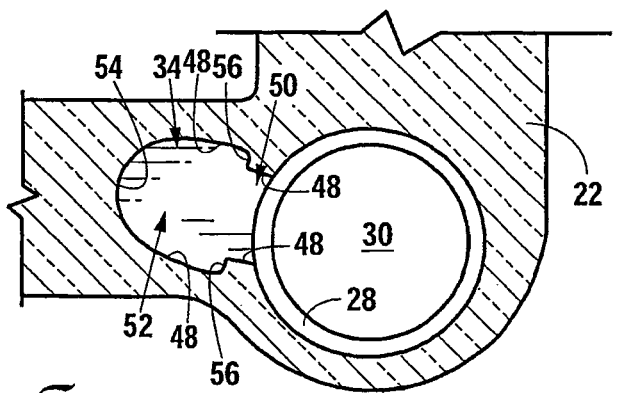
FIG. 4 is a sectional view through line 4-4 of FIG. 3.

FIGS. 2-4 show one of the slots 32 and its corresponding access 34 of FIG. 1 in greater detail. Referring first to FIG. 2, the access 34 is adjacent to the outer surface 24 of the plate 22 and is defined by an access sidewall 40. The access sidewall 40 defines an access passage 42 adjacent to the bore sidewall 28 and an access opening 44 adjacent to the access passage 44 opposite of the bore 30. The access opening 44 terminates at a rounded end 46 distal from the access passage 42.

As shown in FIGS. 3-4, the slot 32 is defined by a slot sidewall 48 and is adjacent to and inward from the access 34. The slot 32 has a slot passage 50 adjacent to the bore sidewall 28 and a slot opening 52 adjacent to the slot passage 50 opposite of the bore 30. The slot sidewall 48 forms a curved end 54 distal from the slot passage 50 and stops 56 positioned between the curved end 54 and the slot passage 50. In relationship to axis of the bore 30, the stops 56 face radially outward from the bore 30.

The profile of the access 34 is smaller than the profile of the slot 32. The width of the access passage 42 is greater than the width of the slot passage 50, forming overhangs adjacent to and outward of the slot passage 50. In addition, the position of the distal end 54 of the slot 32 is further from the bore 30 than the distal end 46 of the access, forming an overhang at the distal end 54 of the slot opening 52.

Figure 5A:
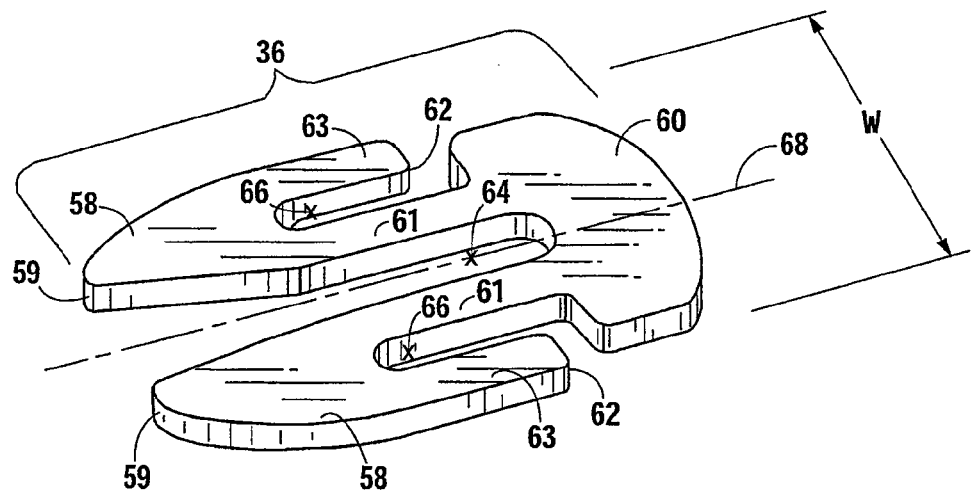
FIG. 5A-5B are isometric views of the retaining clip of FIG. 1 in an open and closed state, respectively.
Figure 5B:
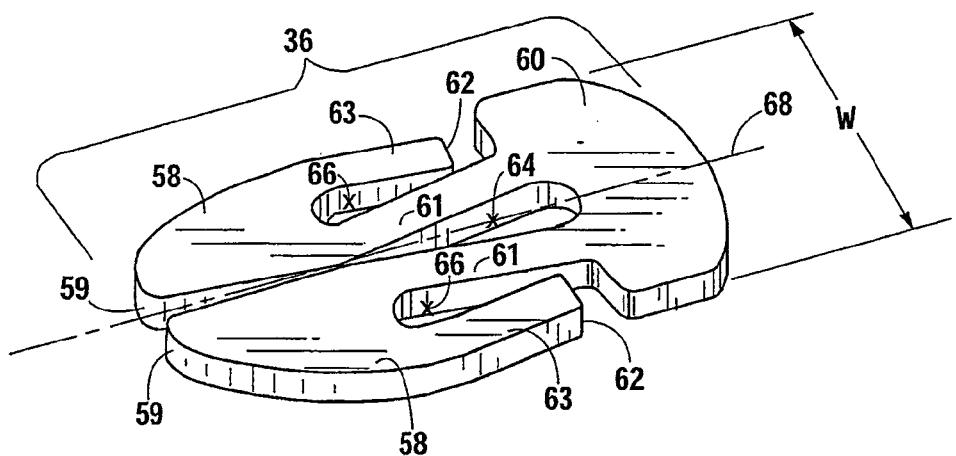

Referring to FIGS. 5A-5B, the retaining member 36 has two U-shaped switchback members 58 extending from a body portion 60. Each U-shaped switchback member 58 has an inner arm 61 joined with an outer arm 63 at an end 59 distal from the body portion 60. The inner arm 61 of each U-shaped portion extends from the body portion 60. The outer arms 63 extend from the distal end 59 toward the body portion 60 and terminate at outer arm ends 62. A center bending moment 64 is positioned between the U-shaped switchback members 58, and outer bending moments 66 are located between each pair of inner and outer arms 61, 63.

The retaining member 36 is bendable around the center bending moment 64 and outer bending moments 66 between a normally-open position, shown in FIG. 5A, and a closed position, shown in FIG. 5B. In the open position, the overall width W of the retaining member 36 is larger than the width of the slot passage 50. In the closed position, the inner arms 61 of the U-shaped switchback members 58 are in contact along a longitudinal centerline 68 of the retaining member 36, and the outer arms 63 are bent around the outer bending movements 64 toward the centerline 68. In the closed position, the retaining member 36 has a width W less than, and can move through, the slot passage 50.

Figure 6A:
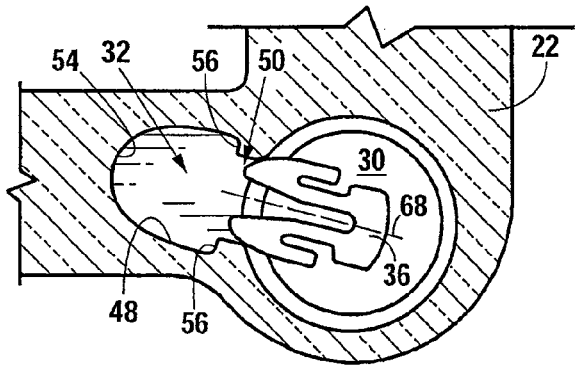
FIGS. 6A-6C are views of the retaining clip of FIG. 5 in various degrees of insertion into the slot shown in FIG. 4.
Figure 6B:
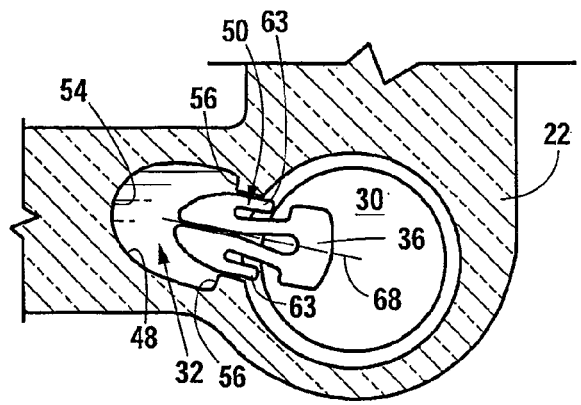
Figure 6C:
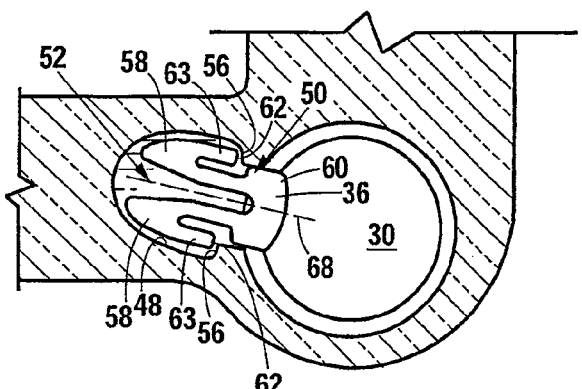

FIG. 6A-6C show the retaining member 36 in pre-inserted, partially inserted, and fully-inserted positions, respectively, with respect to the slot 32. The view is the same as that of FIG. 5. In the pre-inserted position of FIG. 6A, the retaining member 36 is positioned within the bore 30 and aligned with the slot passage 50. Thereafter, the retaining member 36 may be moved into the slot 32 from the bore 30.

In FIG. 6B, the outer arms 63 are in contact with the portion of the slot sidewall 48 defining the slot passage 50, which forces the U-shaped switchback members 58 toward the centerline 68 as the retaining member 36 is moved into the slot 32.

When the retaining member 36 is fully inserted into the slot 32, as shown in FIG. 6C, the outer arm ends 62 are positioned in the slot opening 52 and the outer arms 63 are expanded outward and contact the slot sidewall 48. The body portion 60 of the retaining member 36 is partially positioned in the bore 30. In this position, movement of the retaining member 36 out of the slot 32 toward the bore 30 is impeded by engagement of the arm ends 62 with the stops 56 formed by the slot sidewall 48. Outward movement of the retaining member 36 from the slot 32 (i.e., toward the outer surface 24) is impeded by the overhangs resulting from the differing profiles of the access 34 and the slot 32, as described with reference to FIGS. 2-4.

Figure 7A:
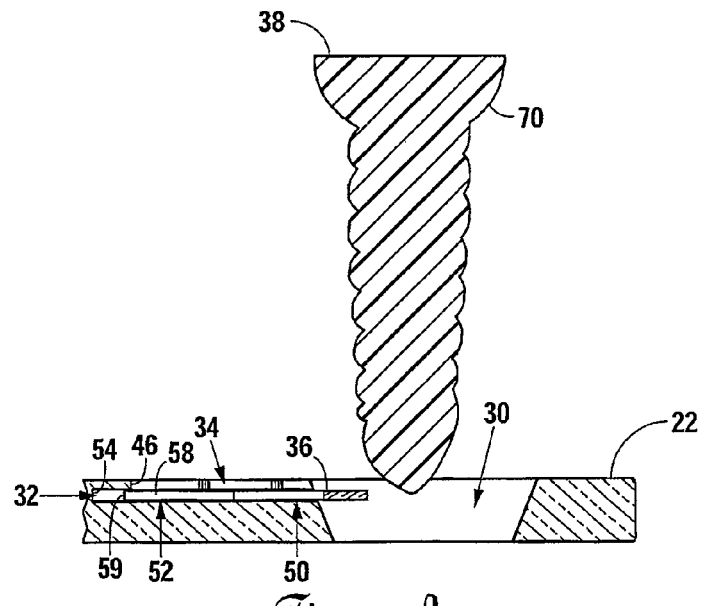
FIG. 7A-7C are views of the bone screw of FIG. 1 in various degrees of insertion into the bore shown in FIGS. 6A-6C.
Figure 7B:
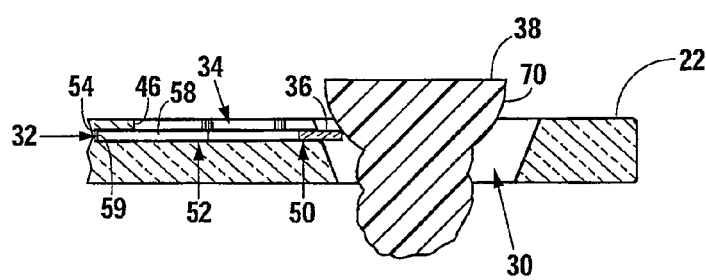
Figure 7C:
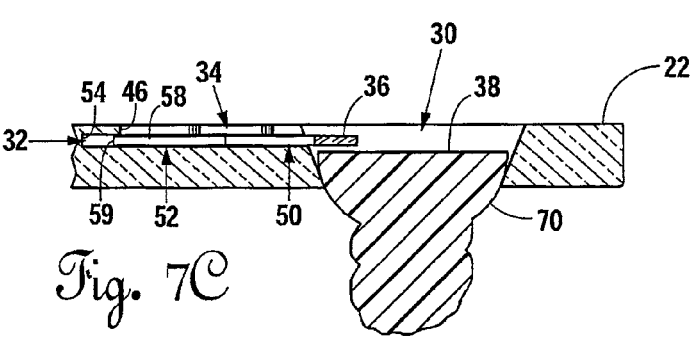
Figure 8:
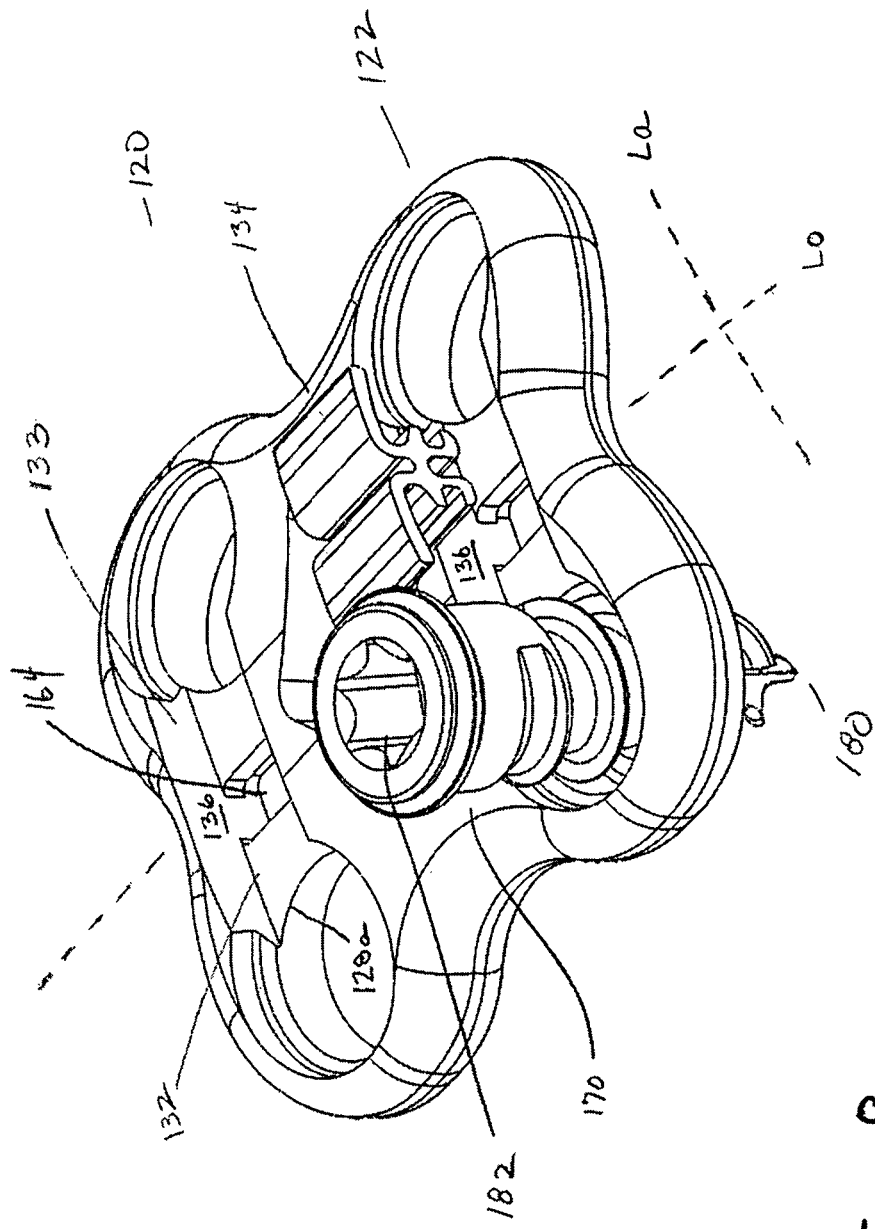
FIG. 8 is a perspective view of another embodiment of Applicant's bone fixation assembly.

Use of the embodiment is described with respect to FIGS. 7A-7C. Referring to FIG. 7A, the retaining member 36 is first positioned in the slot 32. During the medical procedure, the corresponding bone screw 38 is aligned with and inserted into the corresponding bore 30. Referring to FIG. 7B, as the screw 38 is driven inward, the curved shape of the screw head 70 exerts force against the body portion 60 of the retaining member 36 further into the slot 32, causing contact of the distal ends 59 of the U-shaped switchback member 58 with the sidewall 48 and distal end 54 of the slot opening 52, which results in bending of the retaining member 36 around the center bending moment 64 (see FIGS. 5A-5B). The Nitinol properties of the retaining member 36 facilitate this bending action.

Referring to FIG. 7C, as the screw head 70 is driven inwardly of the slot 32, the elastic retaining member 36 expands against the curved distal end 54 and urge the retaining member 36 toward the bore 30 and back to its position shown in FIG. 7A so that the body portion 60 extends into the bore 30 outwardly of the screw head 70. In this position, back out of the screw 38 is limited by the position of the body portion 60 in the bore 30.

Referring back to FIGS. 6A-6C, if necessary, the retaining members 36 can be removed by grasping the U-shaped members 58 of the retaining member 36 through the access 34 and bending the retaining member 36 to the closed position, shown in FIG. 5B. In the closed position, the retaining member 36 is narrower than the slot passage 50, and the retaining member 36 can be moved into bore 30 through the slot passage 50.

The bone screws 38 may be removed using a driver having a cam feature that forces the retaining member 36 into the slot 32 while the screw 38 is reversed out of the bone. As the screw 38 is turned, the cam feature forces the body portion 60 of the retaining member 36 out of the bore 30 and into the slot 32 so that the outer portion of the screw head 70 can move outward of the slot 32. As the screw 38 backs out of is fastening engagement with the patient's bone to the position of the retaining member 36, the screw head 70 will hold the retaining member 36 in the slot 32 and allow further loosening of the screw 38.

FIGS. 8-13 illustrate and set forth a second embodiment of Applicant's bone fixation assembly embodiment 120. Embodiment 120 includes a bone fixation plate 122 having an outer having an outer surface 124 and a bone contact surface 126. Bore side walls 128 are provided defining bores 130 therein. Applicant's bone fixation assembly 120 may have a longitudinal axis Lo and a lateral axis La substantially perpendicular thereto (see FIG. 8). Generally, embodiment 120 of bone fixation assembly is seen to have a tab 134, which is configured to engage an opening between laterally adjacent bores 130, as set forth in more detail below. Tab 134 includes a pair of opposed plates 138/140, which trend generally laterally outward along a lateral axis substantially perpendicular to the longitudinal axis, which opposed plates 138/140 are typically generally resilient and tabular. Tabular means having a length and width that of a similar order of magnitude, but a thickness that is a smaller order and magnitude or at least substantially smaller, than the length and width. In one embodiment, the shorter of the length or the width is about 5 to 10 times the thickness.

A depending anchor portion 142 is configured to anchor tabs 138/140, so that they extend laterally into tab openings 132/133 in a manner set forth in more detail below. Functionally, anchor portion 142 is designed to positionally maintain opposed plates 138/140 substantially suspended in tab openings 132/133, such that the plates are not touching or interfered with by bone fixation plate 122.

Figure 13:
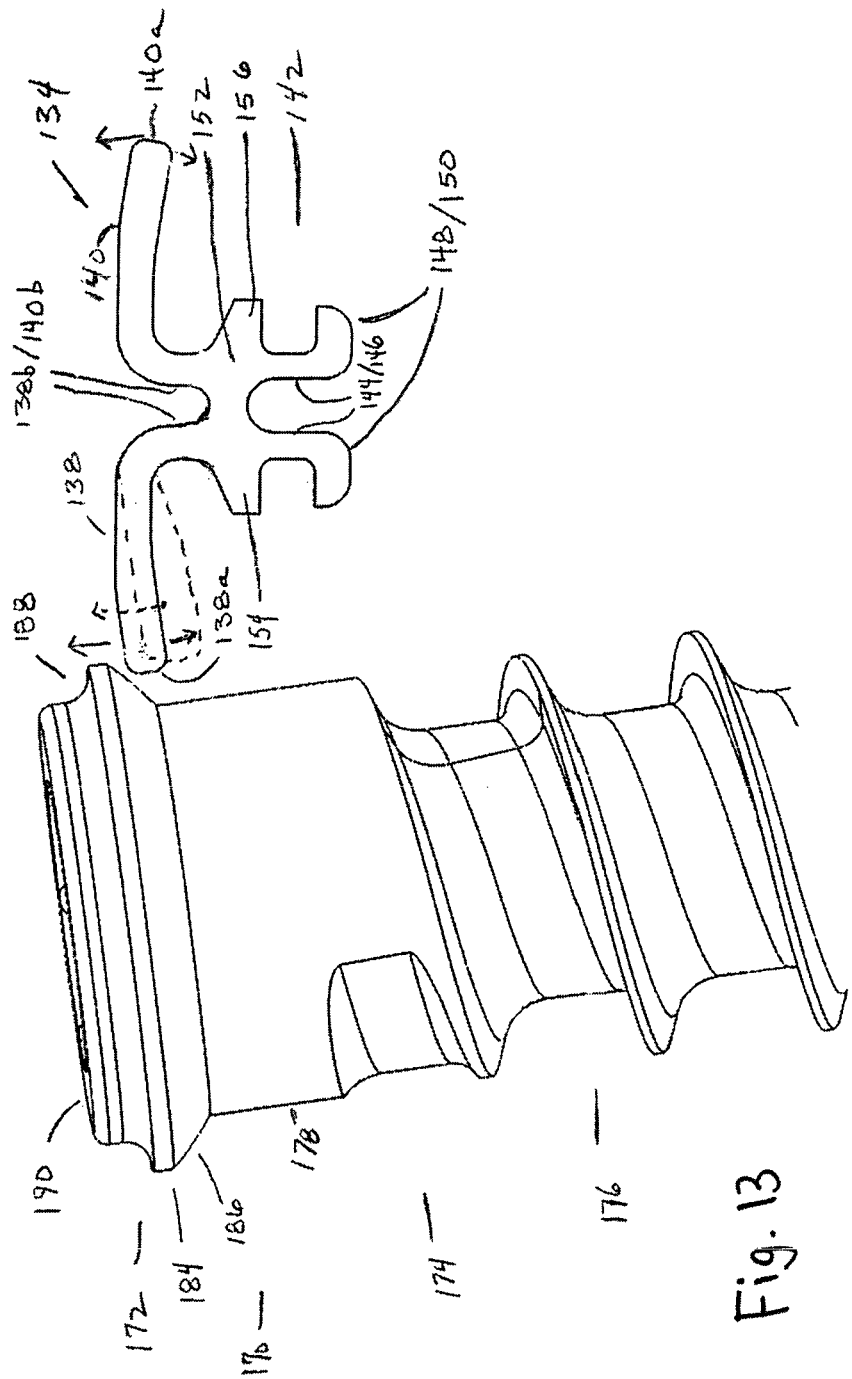
FIG. 13 is a detailed view of part of the assembly of the embodiment of FIG. 8 without the bone plate.

Plates 138/140 are configured with leading edges 138*a*/140*a* that are removed from the longitudinal axis (and typically about parallel thereto) and trailing edges 138*b*/140*b* with which are close to, adjacent or on the longitudinal axis and attached to anchor portion 142. The lateral distance between the trailing edge attachment at the anchor portion and the leading edge is sufficient to provide a sufficient movement arm to accomplish the bending as set forth herein. Screws 170 are adapted to be received through bore 130 advancing until a head 172 of the screw engages at least a portion of leading edges 138*a*/140*a*, causing them to flex or bend downward in the direction of the down arrow indicated in FIG. 9. Upon passage of the screw head past the leading edges, they (being resilient) will rebound ("up" arrow, FIG. 9), so they are in the undeflected or locked position, the leading edges preventing the backing out of the screw. This is seen in FIG. 13, showing plate 138 with leading edge 138*a* in a normal undeflected or locked position (solid lines) and in dotted lines bending downward responsive to the passage of the screw head there past. It is seen that tab opening 132/133 opens partially into bores 130 and that bore side walls 128 typically include an undercut portion 128*a*, which allows the leading edges of the tabs to extend into the bores.

Turning back to FIGS. 9, 12, and 13, it is seen that the configuration of tab anchor portion 142 is to depend from the trailing edge 138*b*/140*b* of the opposed plates and to securely engage the plates so that they are fixed thereto and to engage the opposed plates 138/140, such that the plates are substantially free to move in the flexed position as set forth above without interference with the bone fixation plate 122.

Anchor portion 142 is seen to achieve the anchoring function, in one embodiment, by having a pair of adjacent generally parallel depending legs 144/146 extending below a body 152. Feet 148/150 may extend generally perpendicular and outward from the removed ends of the legs. In one embodiment, body 152 of anchor portion 142 is seen to have lateral arms 154/156 that extend outward therefrom. The configuration of anchor portion 142 along with the configuration of an opening for receipt thereof, and engagement of the anchor portion with bone fixation plate 122 provides a fairly solid and rigid coupling of the tabs to the bone fixation plate 122, so as to provide an anchor for opposed plates 138/140.

Turning back to tab openings 132/133, it is seen that a pair of opposed side walls 136 having portions 136a/136b provides a sufficient opening for opposed plates 138/140, such that the side walls of the opposed plates represented by 136a/136b are free to move without interference. Tab openings 132/133 also include tab floor portions 158/160 that are deep enough with respect to outer surface 124 of bone fixation assembly, so that the underside of the opposed plates 138/140 may pivot or bend without contacting the tabs. Thus, a gap 153 is provided between the undersides of plates 138/140 and floor portion 158/160 (see FIG. 12). Tab openings 132/133 are also configured with first (leg) cutouts 162 having lateral walls 162a/162b which are sufficiently spaced apart to snugly receive legs 144/146. Indeed, the legs and feet are somewhat resilient so there may be some flexing as the legs and feet pass through first cutout 162 (during installation of the tabs to the bone anchor plate), such that the legs are urged against lateral walls 162a/162b. Second cutout 164 is seen to have portion 164a/164b that represent cutout positions of the bone fixation plate for snug and typically resilient receipt of feet 148/150 thereinto.

Figure 9:
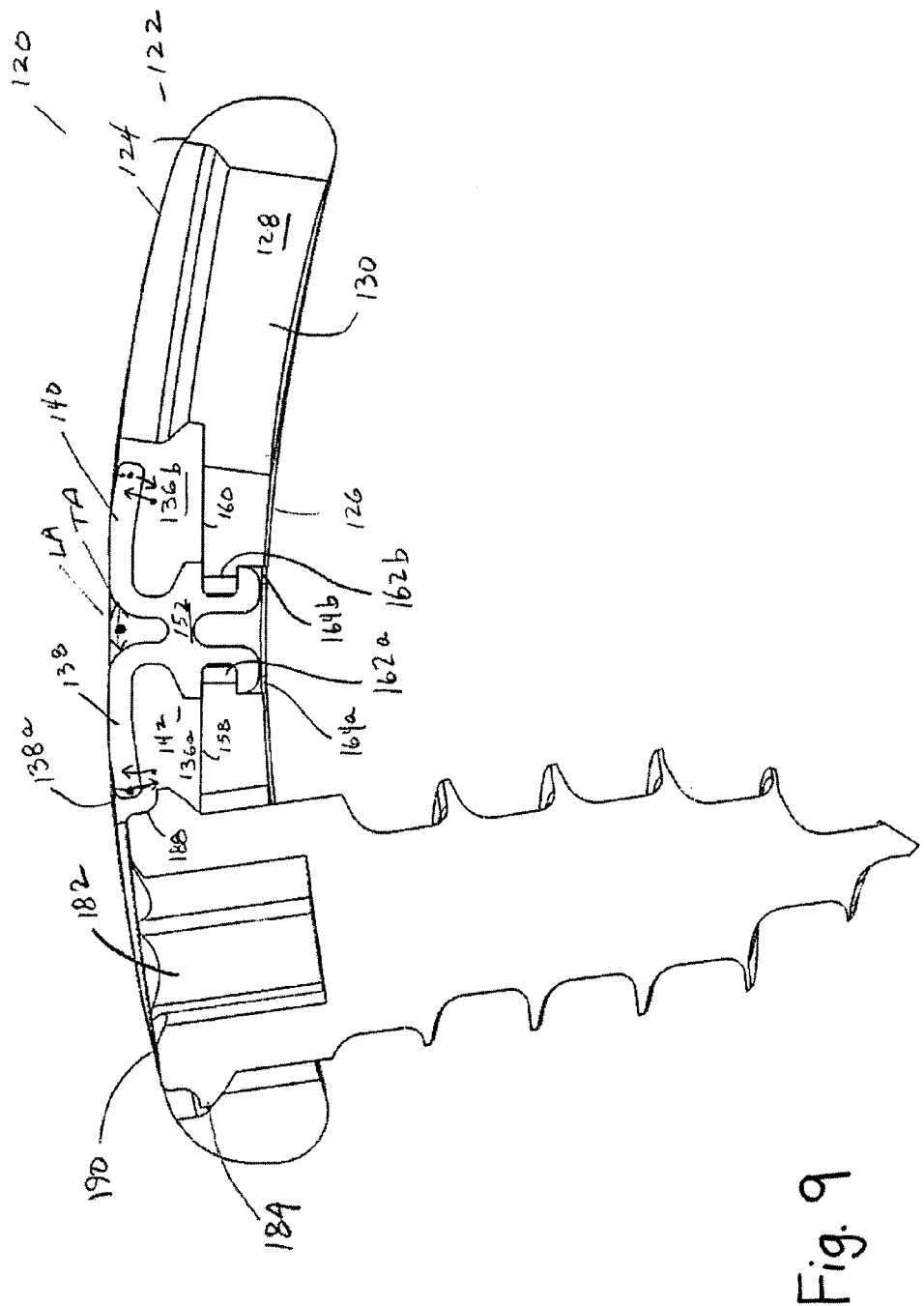
FIG. 9 is a cross-sectional view of the embodiment of FIG. 8.
Figure 10:
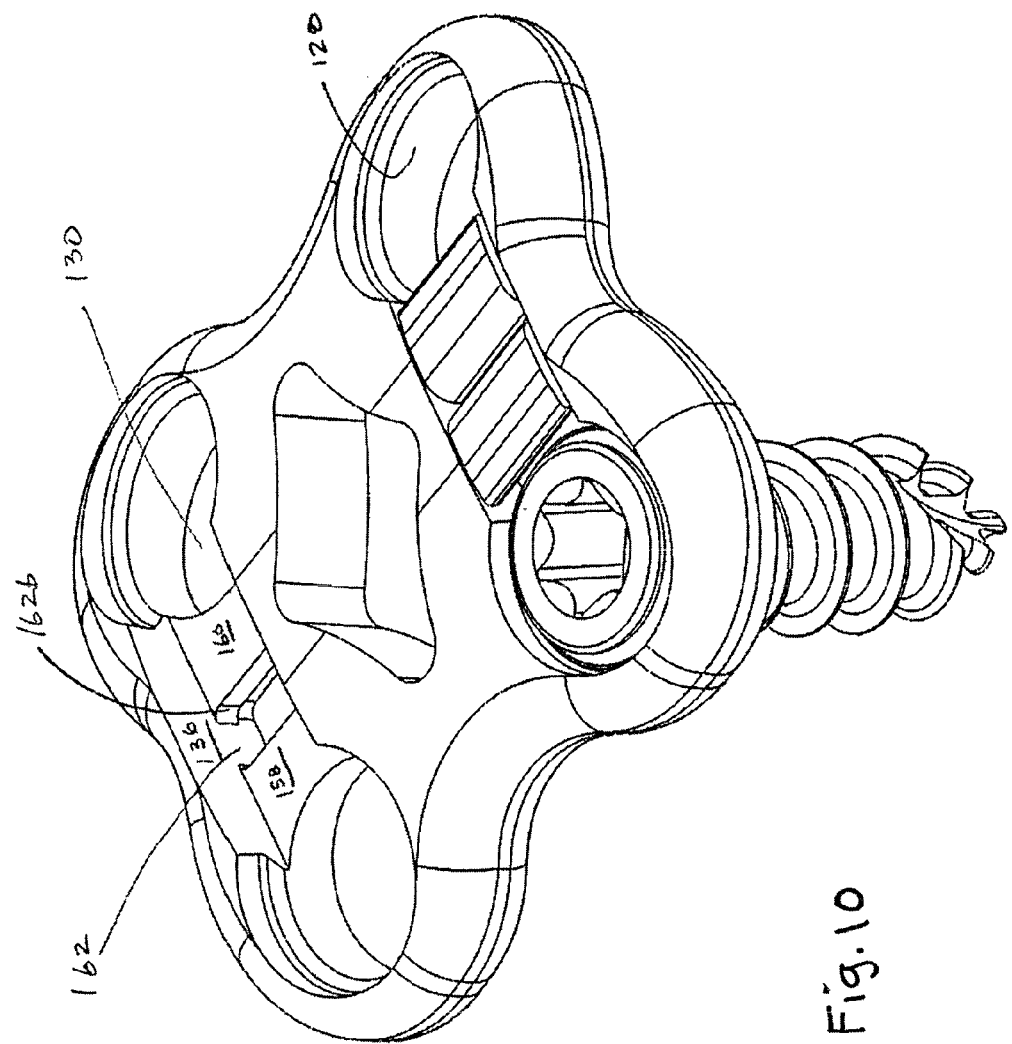
FIG. 10 is another perspective view of the embodiment of FIG. 8.
Figure 11:
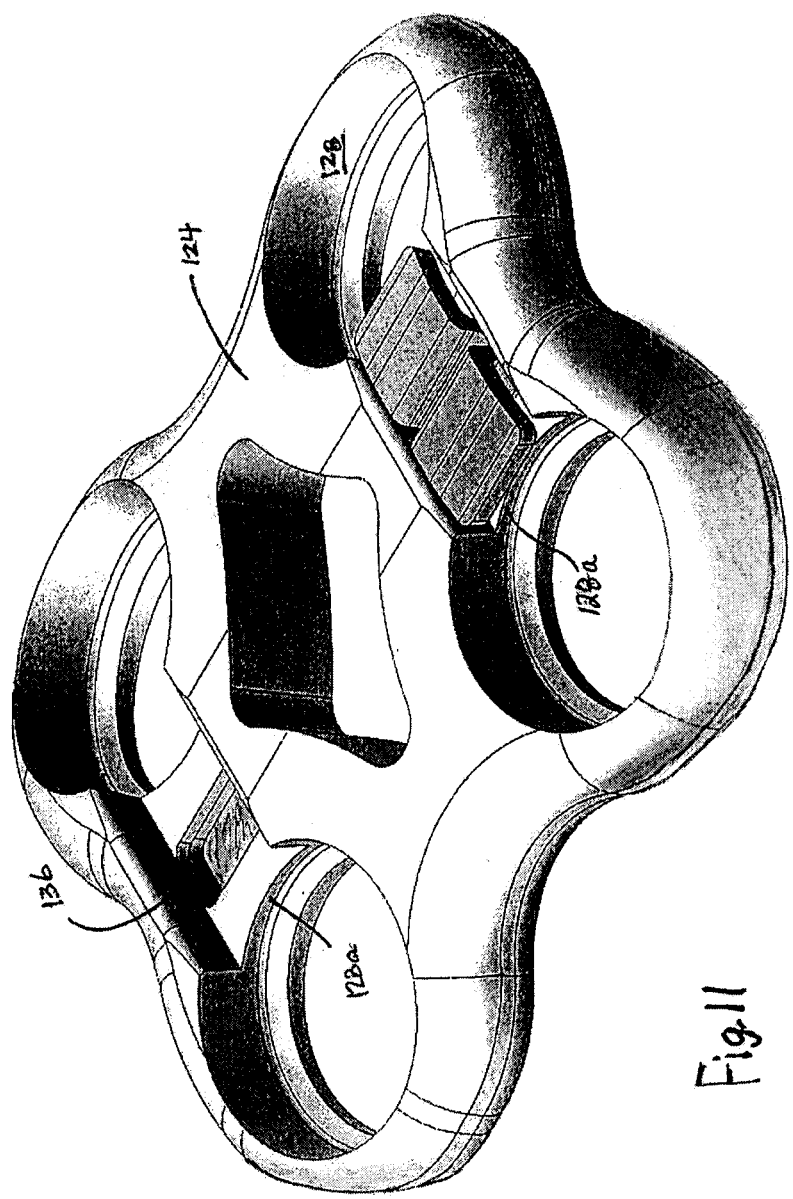
FIG. 11 is another perspective view of the embodiment of FIG. 8.
Figure 12:
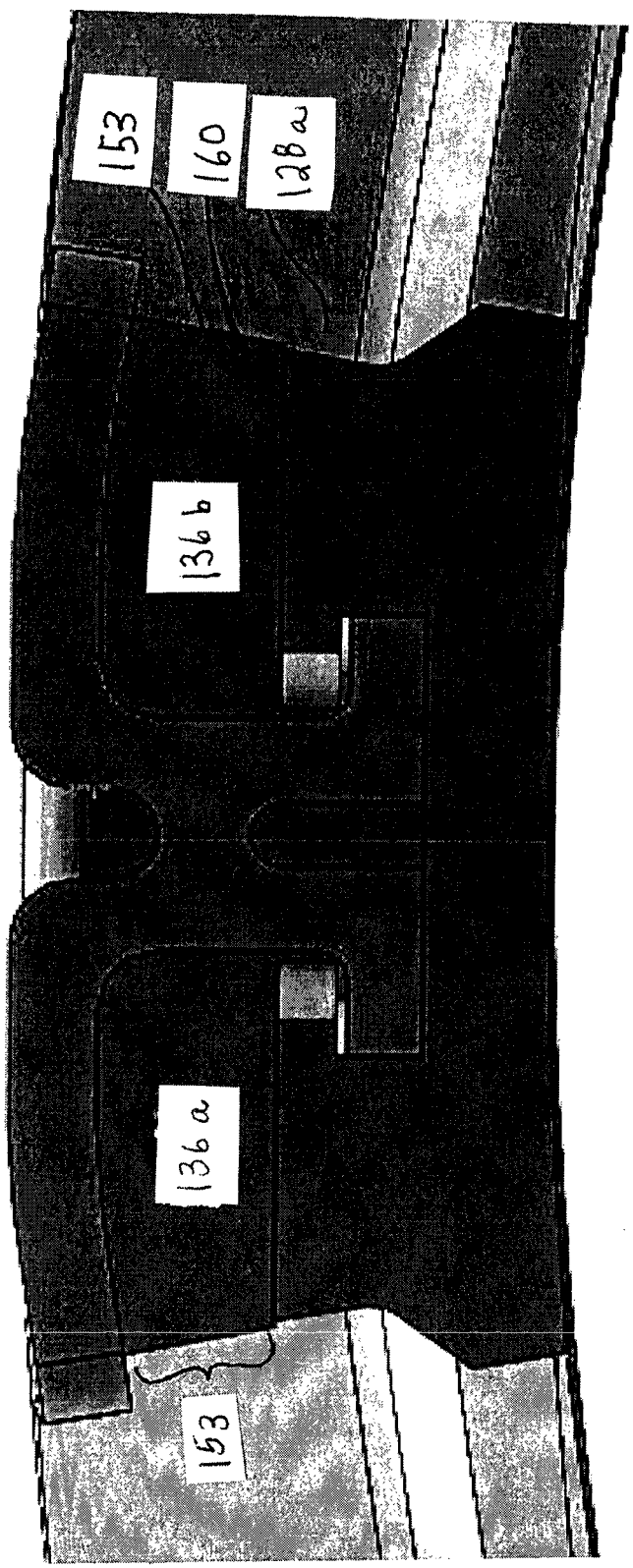
FIG. 12 is a partial cross-sectional view of the embodiment of FIG. 8.

In one embodiment, the legs and feet are typically resilient enough such that, during installation of the tabs, they may be flexed slightly to slip into first and second cutouts (legs and feet), such that there is a snug and resilient fit with snug contact between the C-shape outline or bay defined by lateral arms 154/156, legs 144/146, and feet 148/150 about the projection defined by side walls 162a/162b. As best seen in FIG. 9, the close coupling of the legs and feet with side walls 162a/162b can be seen and such coupling allows the anchor portion to provide for the positioning of opposed plates 138/140 in the opening to the bore side walls 128 defined by tab openings 132/133.

Screw 170 is seen to have a head 172 at an upper end thereof and a shank 174 depending therefrom. Shank 174 may include a threaded portion 176 (for engaging bone) and a smooth portion 178, and may terminate at a conical or pointed tip 180. The head may define a lip 184 that has a larger diameter than where the shank and head meet. Below lip 184, inclined walls 186 are at least partially conical and depend to where head 172 meets shank 174 and provide a surface across which the leading edges 138a/140a will flex as screw 170 is advanced into the bone with bone fixation plate 122 adjacent the upper surface of the vertebral bodies. Lip 184 has recessed walls 188 that diminish in diameter and a top wall, typically perpendicular to the longitudinal axis of the screw and containing a tool engaging recess 182, such as a slot or star or other tool engaging recess for advancing the screw into the bone. It is seen with respect to FIG. 9 that the bone plate bore side walls 128 are configured to allow lip 184 to pass the outer surfaces, but stop when it is below the leading edge, and the top wall 190 is about flush with outer surface 124. The assembly or parts thereof may be made from titanium, nitenol, stainless steel or any other suitable material or combination of materials. The bone fixation plate may span two or more levels and will have a slight curve (see FIG. 9).

The present invention is described in terms of a preferred illustrative embodiment of specifically-described bone fixation assembly. Those skilled in the art will recognize that yet other alternative embodiments of such an assembly can be used in carrying out the present invention. Other aspects, features, and advantages of the present invention may be obtained from a study of this disclosure and the drawings, along with the appended claims.

The invention claimed is:

1. A bone fixation assembly comprising:
   a bone fixation plate having an outer surface, a bone contact surface, and at least one bore sidewall defining at least one bore extending between said outer surface and said bone contact surface, said outer surface being located outwardly of said bone contact surface;
   at least one slot sidewall defining at least one slot formed in said bone fixation plate, said at least one slot being adjacent to said at least one bore sidewall and between said outer surface and said bone contact surface, said at least one slot having at least one slot passage adjacent to a corresponding bore and a slot opening adjacent to said slot passage;
   at least one stop formed by said at least one slot sidewall, said at least one stop positioned opposite of said slot passage from the corresponding bore; and
   at least one retaining member insertable into said at least one slot from said at least one bore, wherein said at least one retaining member is bendable between a normally-open position having a width greater than the width of said at least one slot passage and a closed position having a width less than the width of said slot passage.

2. The bone fixation assembly of claim 1 further comprising at least one access sidewall inward of said outer surface and defining at least one access to said at least one slot, said at least one access being located outwardly from said at least one slot.

3. The bone fixation assembly of claim 2 wherein said at least one access sidewall defines an access passage adjacent to said corresponding bore and an access opening adjacent to said access passage.

4. The bone fixation assembly of claim 2 wherein said at least one slot is adjacent to said outer surface.

5. The bone fixation assembly of claim 1 wherein said at least one retaining member comprises at least one switchback member having inner and outer arms joined at a distal end, said at least one switchback member extending from a body portion.

6. The bone fixation assembly of claim 5 further comprising a center bending moment positioned between said at least one switchback member, and outer bending moments located between the inner and outer arms of said at least one switchback member.

7. The bone fixation assembly of claim 5 wherein said at least one switchback member is U-shaped.

8. The bone fixation assembly of claim 5 wherein said at least one switchback member J-shaped.

9. The bone fixation assembly of claim 5 further comprising:
   at least one bone screw insertable into said at least one bore, said at least one bone screw having a hemispherical head engageable with said bore sidewall to anchor said bone plate to a patient's bone; and wherein said at least one retaining member is positioned in said at least one slot with said outer arms positioned in said slot opening and at least a portion of the retaining member extending into said at least one bore outwardly of the bone screw.

\* \* \* \* \*